United States Patent [19]

Renga et al.

[11] 4,413,137

[45] Nov. 1, 1983

[54] PROCESS FOR MAKING VICINAL EPOXIDES

[75] Inventors: James M. Renga, Midland, Mich.; Roy A. Periana-Pillai, Berkeley, Calif.

[73] Assignee: The Dow Chemical Company, Midland, Mich.

[21] Appl. No.: 390,438

[22] Filed: Jun. 21, 1982

[51] Int. Cl.³ .................... C07D 301/02; C07C 17/33; C07C 19/045
[52] U.S. Cl. ..................................... 549/518; 570/261
[58] Field of Search ........................ 549/518; 570/261

[56] References Cited

U.S. PATENT DOCUMENTS

| 4,261,906 | 4/1981 | Renga et al. | 549/518 |
| 4,349,482 | 9/1982 | Renga et al. | 549/518 |
| 4,371,704 | 2/1983 | McEntire et al. | 549/518 |

FOREIGN PATENT DOCUMENTS 53-46921  4/1978  Japan .

Primary Examiner—Norma S. Milestone
Attorney, Agent, or Firm—Douglas N. Deline

[57] ABSTRACT

Vicinal epoxides and an alkylene dihalide are prepared by contacting a mixture comprising ethylene carbonate and a β-haloalkyl carbonate with an initiator at a temperature from about 25° C. to about 260° C.

10 Claims, No Drawings

PROCESS FOR MAKING VICINAL EPOXIDES

BACKGROUND OF THE INVENTION

The present invention relates to a new process for the preparation of vicinal epoxides and alkylene dihalides.

In U.S. Pat. No. 4,261,906 it was disclosed that unsymmetrical β-haloalkyl carbonates may be decomposed by heating in the presence of quaternary ammonium or phosphonium salts thereby forming vicinal epoxides and halogenated alkanes.

It is known that cyclic carbonates may be decomposed to form epoxides in the presence of various catalysts. Such a process particularly directed to the preparation of propylene oxide by decomposition of propylene carbonate in the presence of a sulfonium or phosphonium halide or any of certain metal salts is described in U.S. Pat. No. 4,069,234.

SUMMARY OF THE INVENTION

According to the present invention, vicinal epoxides and halogenated alkane by-products are formed in increased yield and selectivity by contacting a mixture comprising a β-haloalkyl carbonate and ethylene carbonate with a small but effective amount of an initiator at a temperature from about 25° C. to about 260° C.

DETAILED DESCRIPTION OF THE INVENTION

The β-haloalkyl carbonates employed according to the invention are those corresponding to the formula:

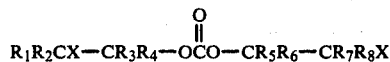

where:
each $R_1$–$R_8$ independently is hydrogen, a hydrocarbon group of up to about 20 carbons, —$CH_2X$ or —$CH_2Y$ where Y is an alkoxy group of up to 10 carbons, preferably of 1–4 carbons, or an aroxy group of up to about 20 carbons, such as a phenol or bisphenol residue; and
X is chloro or bromo;
provided that at least one of $R_1$–$R_8$ is not hydrogen.

Thus the vicinal epoxide products formed according to the invention corresponds to the formula:

Preferably X is chloro and each $R_1$–$R_8$ is either hydrogen, $C_{1-4}$ alkyl or haloalkyl or phenyl. Most preferred β-haloalkyl carbonates for use according to the present invention are 2-chloroethyl β-haloalkyl carbonates such as 2-chloroethyl 1-chloro-2-propyl carbonate and 2-chloroethyl 1,3-dichloro-2-propyl carbonate which may be employed to prepare propylene oxide and epichlorohydrine.

The β-halogenated alkyl carbonate starting materials for this process can be prepared by several known procedures. The reaction of a chloroformate with an alcohol conventionally used for the preparation of carbonate esters is readily adapted to the preparation of these halogenated carbonates by using the appropriate halogenated alcohol and halogenated alkyl chloroformate reactants. Symmetrical bis(haloalkyl)carbonates in particular can be made by the strong acid catalyzed transesterification reaction of a halogenated alcohol in excess with a dialkyl carbonate. Some of these carbonates can also be made by using an appropriate unsaturated alcohol in the transesterification reaction and then adding halogen or hydrogen halide to the unsaturated ester product. A method recently described in Japanese Pat. 46,921/78 whereby a cyclic carbonate such as ethylene carbonate or propylene carbonate is reacted at moderate temperature with an olefin and chlorine or bromine in equal molar amounts is another means of obtaining the halogenated alkyl carbonate starting materials of this invention. By using ethylene carbonate (which is made from ethylene oxide) and an olefin other than ethylene as reactants in the cited Japanese process to make the haloalkyl carbonate starting material of this invention, the present process becomes essentially a means for transferring the epoxide value of ethylene oxide to higher olefins using organic carbonates as intermediates. For the teachings contained therein, Japanese Pat. No. 46,921/78 is hereby incorporated in its entirety by reference.

The use of the present invention to prepare a vicinal epoxide from a β-halogenated alkyl carbonate is particularly useful when employed in combination with the process of the above Japanese Pat. No. 46,921/78 where ethylene carbonate is employed as the cyclic carbonate reactant. Advantageously, the ethylene carbonate need not be separated from the β-haloalkyl carbonate prior to use in the present invention thereby avoiding the need for difficult and costly purification steps in the synthetic procedure. Additionally, and surprisingly, it has been found that improved selectivities to the desired substituted epoxide

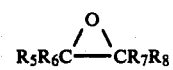

are achieved by the presence of ethylene carbonate in the reaction mixture of the present invention.

Suitable initiators for use according to the present process include alkali metal halides, optionally in the presence of a solubilizing agent such as a phase-transfer catalyst, e.g., hexamethylene phosphoramide or crown ethers such as the cyclic polymers of ethylene oxide. Additional suitable initiators include monomeric or polymeric chelating agents containing a group V element, particularly nitrogen or phosphorus. Preferred chelating agents are compounds containing polar nitrogen or phosphorus functionality, e.g., amines, amides, phosphines, phosphoramides and phosphine oxides. Suitable examples include cyclic saturated or unsaturated nitrogen-containing compounds such as pyridines, pyrazines, triazines, tetrahydropyridines, pyrroles, imidazoles, pyrrolidines, imidazolines, oxazolidines, pyrrolidinones, etc.; aliphatic amine compounds such as ethylene diamine, tetraethylene pentamine, etc.; and phosphorus compounds such as trialkyl- or triphenylphosphines or phosphine oxides, etc.; and combinations of phosphorus- and nitrogen-containing compounds, e.g., hexaalkylphosphoramides. Preferred chelating agents are N-methyl-2-pyrrolidinone, triphenylphosphine and hexamethylphosphoramide. It is noted further than the latter class of chelating agents may additionally serve as solubilizing agents in the presence of inorganic salt initiators.

Further suitable initiators include quaternary ammonium or phosphonium salts. Preferably these salts have the formula $R'_4AY$ where each $R'$ is a hydrocarbon moiety; A is a quaternized nitrogen or phosphorus atom; and Y is an inert (i.e., inert in this process) neutralizing anion that may be inorganic, e.g., chloride, bromide, iodide, bicarbonate, sulfate, or the like; or Y may be an organic ion such as formate, acetate, benzoate, phenate, or bisphenolate. The R groups may be alkyl, aryl, alkaryl, aralkyl, or cycloalkyl. Also, two R groups may combine to form a heterocyclic ring. Illustrative quaternary salt catalysts are tetrabutylammmonium bromide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and corresponding ammonium and phosphonium salts with these and other such inorganic and organic neutralizing anions as described above. The catalytic salt may be added as such to the reaction mixture or it may be formed in situ.

In a mode of the invention particularly adapted to continuous operation, one or more $R'$ groups may be pendant methylene groups from a resin matrix so that the quaternary salt is a salt form of a strong base anion-exchange resin such as DOWEX ® 21K, DOWEX ® 11, DOWEX ® MSA-1, or other such commercially available ion-exchange resins or the phosphonium equivalents of such quaternary ammonium-substituted resins. In such a continuous operation of the process, the β-haloalkyl carbonate starting material can be passed at an appropriate flow rate through a bed of the strong base anion resin maintained at a suitable temperature within the limits previously defined. Similarly, a solid particulate catalyst can be formed by depositing a quaternary ammonium or phosphonium salt as described above on silica, alumina, clay, a zeolite, or other such inert support.

Additional suitable initiators include bases such as alkali metal hydroxides or alkoxides, and salts of strong bases and weak acids such as alkali metal carbonates or bicarbonates.

A reaction solvent or diluent is usually of no advantage and the process is ordinarily run in the absence of such an inert additive. In some cases, however, a solvent may be of some advantage. Inert solvents suitable for use include hydrocarbons such as toluene, xylene, and decane; glycol diethers such as dimethyloxyethane, substituted amides such as N,N-dimethylformamide, and cyclic compounds such as tetrahydrofuran and sulfolane.

The preferred initiator is lithium chloride, which in the presence of ethylene carbonate, efficiently initiates the present process without the use of a solubilizing agent.

The initiator is added in an effective amount. Generally, from about 0.1 to about 10 mole percent of the initiator based on total carbonate reactants is sufficient. Where a solubilizing agent is additionally employed, it is generally employed in about a 1:1 to about 3:1 molar ratio with the initiator compound.

The amount of ethylene carbonate present in the reaction may vary within rather wide limits. Suitably from about 0.1 to about 10 moles for each mole of β-haloalkyl carbonate compound is sufficient. Preferably about 0.5 mole to about 2 moles of ethylene carbonate are present for each mole of β-haloalkyl carbonate compound.

Within the temperature range provided best results are generally obtained at a temperature from about 150° C. to about 250° C. The reaction time under such conditions generally varies from a few minutes to several hours depending on the reactants, temperature and degree of conversion desired. The process may be conducted either continuously or in a batch mode. While elevated pressures may be employed, if desired, no benefit is known to result thereby.

In the preparation of higher boiling epoxides particularly, separation of epoxide products from the reaction mixture may be facilitated by running the reaction under appropriately reduced pressure or by passing a stream of nitrogen or other inert gas through or over the reaction mixture.

The present invention has several advantages over previously known processes. As previously explained, due to the presence of ethylene carbonate in the process, alkali metal halide initiators may generally be employed without the need of extra solubilizing agents. The process additionally greatly increases the selectivity of formation of substituted vicinal epoxides when suitable β-haloalkyl carbonate reactants are employed.

SPECIFIC EMBODIMENTS

Having described the invention, the following examples are provided as further illustrative and are not to be construed as limiting.

EXAMPLE 1

Preparation of Propylene Oxide

A mixture of 2-chloroethyl 1-chloro-2-propyl carbonate (10.05 g., 50.0 mmoles), ethylene carbonate (4.4 g, 50.0 mmoles), triphenylphosphine (0.66 g, 2.5 mmoles) and lithium chloride (0.1 g, 2.5 mmoles), was charged to a 50-ml reaction flask equipped with a mechanical stirrer, condenser, receiver and cold trap (dry ice/acetone). The receiver contained 50 ml toluene and 2.0 ml of tetrahydrofuran which was the internal standard for gas chromatographic analysis. After heating with an oil bath to 180° C. for 3.5 hours, greater than a 99 percent conversion of carbonate was observed. Gas chromatographic analysis gave a 52 percent yield of ethylene oxide and an 83 percent yield of propylene oxide together with a 73 percent yield of ethylene dichloride and a 2 percent yield of propylene dichloride. Also formed were a 14 percent yield of ethylene chlorohydrin and a 3 percent yield of propylene chlorohydrin (possibly due to water present in the starting materials) and a 24 percent yield of acetaldehyde (due to a rearrangement of the ethylene carbonate).

EXAMPLE 2

Comparative

The reaction conditions of Example 1 were substantially repeated excepting that ethylene carbonate was omitted. Only a 65 percent yield of propylene oxide was obtained together with a 5 percent yield of ethylene oxide, a 74 percent yield of ethylene dichloride, and an 8 percent yield of propylene dichloride. Therefore, in order to maximize the yield of propylene oxide it is beneficial to have ethylene carbonate present.

EXAMPLES 3–7

The reaction conditions of Example 1 were substantially repeated. Accordingly, 2-chloroethyl 1-chloro-2-propyl carbonate (10.05 g, 50.0 mmoles) was heated at 180° C. in the presence of ethylene carbonate and the various initiators further identified in Table I. After the reaction periods indicated, the reaction was stopped and the percent conversion of 2-chloroethyl 1-chloro-2-propyl carbonate as well as product selectivity to propylene oxide were calculated. Results are contained in Table I.

TABLE I

| Example | EC[1] mmoles | initiator | (mmoles) | Reaction Time (hr) | Conversion (%) | Selectivity (%) |
|---|---|---|---|---|---|---|
| 3 | 50 | φ₃P[2]/LiCl[3] | 2.5/2.5 | 3 | >99.0 | 94 |
| 4 | 50 | φ₃P[2] | 2.5 | 5 | 81.9 | 63 |
| 5 | 100 | φ₃P[2] | 2.5 | 5 | 91.3 | 68 |
| 6 | 25 | n-Bu₄PCl[4] | 5.0 | 3 | 98.4 | 80 |
| 7 | 50 | n-Bu₄PCl[4] | 5.0 | 3 | >99.0 | 75 |

[1]ethylene carbonate
[2]triphenylphosphine
[3]same initiator originally employed in Example 1, reused for fourth time
[4]tetra n-butylphosphonium chloride

EXAMPLE 7

2-Chloroethyl 1-chloro-2-propyl carbonate was produced in crude yield by reaction of propylene, chlorine and ethylene carbonate substantially according to the procedure of Japanese Patent application No. 46,921/78. A crude mixture comprising 16.7 mmoles of unreacted ethylene carbonate and 24.9 mmoles of 2-chloroethyl 2-chloro-2-propyl carbonate product was obtained after removal of volatiles. The crude reaction product was combined with triphenylphosphine (0.83 mmole) and heated to 180° C. for 3 hours. Conversion was 79.4 percent with 67 percent selectivity to propylene oxide. Small amounts of propylene carbonate were also obtained.

EXAMPLE 8

The reaction conditions of Example 7 were substantially repeated excepting that lithium chloride (0.83 mmole) was employed as the initiator. Conversion after heating for 3 hours at 180° C. was 92.7 percent. Selectivity to propylene oxide was 65 percent.

EXAMPLES 9-14

The reaction conditions of Example 1 were substantially repeated employing the β-haloalkyl carbonates further identified in Table II. The reactions were carried out by heating at about 175° C.–180° C. for about 3 hours. Products were analyzed and results calculated based on gas-liquid chromatographic analysis. Conversions are calculated as percent of β-haloalkyl carbonate converted. Selectivity is percent of desired vicinal epoxide.

TABLE II

| Example | β-halocarbonate | (mmole) | EC[1] (mmole) | Initiator | (mole %) | Vicinal Epoxide | Conversion (%) | Selectivity (%) |
|---|---|---|---|---|---|---|---|---|
| 9 | 1-chloro-2-butyl 2-chloroethyl carbonate[2] | (45.4) | 54.5 | LiCl/HMPA[3] | (5/5) | 1,2-butylene oxide | 100 | 77.0 |
| 10 | erythro-2-chloro-3-butyl 2-chloroethyl carbonate | (25) | 75.0 | LiCl | (2) | 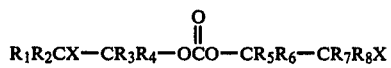 | 100 | 94.3 |
| 11 | threo-2-chloro-3-butyl-2-chloroethyl carbonate | (25) | 75 | LiCl | (2) | 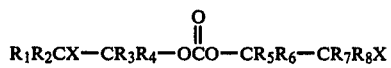 | 100 | 98.5 |
| 12 | 1,3-dichloro-2-propyl 2-chloroethyl carbonate | (25) | 75 | LiCl | (2) | epichlorohydrin[4] | 99.3 | 43.8 |
| 13 | 1-chlorocyclohexyl 2-chloroethyl carbonate | (25) | 75 | LiCl | (5) | 1,2-cyclohexylene oxide[5] | 90.5 | 75.7 |
| 14 | 1-bromocyclohexyl 2-chloroethyl carbonate | (25) | 75 | LiCl | (2) | 1,2-cyclohexylene oxide[5] | 95.0 | 90.0 |

[1]ethylene carbonate
[2]crude devolatilized reaction mixture of butylene, chlorine and ethylene carbonate
[3]hexamethylenephosphoramide
[4]approximately equal amounts of regio isomer 2-chloroethyl 2,3-dichloro-1-propyl carbonate also produced
[5]mechanical stirring and partial pressure of 450 torr. used

What is claimed is:

1. A process for making a vicinal epoxide and an alkylene dihalide which comprises contacting a mixture comprising ethylene carbonate and a β-haloalkyl carbonate corresponding to the formula:

$$R_1R_2CX-CR_3R_4-OCO-CR_5R_6-CR_7R_8X$$

with an initiator at a temperature from about 25° C. to about 260° C., wherein:
each $R_1$–$R_8$ independently is hydrogen, a hydrocarbon group of up to about 20 carbons, —CH₂X or —CH₂Y, where Y is an alkoxy group of up to 10 carbons or an aroxy group of up to about 20 carbons; and
X is chloro or bromo.

2. The process of claim 1 wherein the temperature is from about 150° C. to about 250° C.

3. The process of claim 1 wherein the initiator is an alkali metal halide, a monomeric or polymeric chelating agent containing a group V element, a quaternary ammonium or phosphonium salt, a base or a salt of a strong base and a weak acid.

4. The process of claim 3 wherein the initiator is an alkali metal halide.

5. The process of claim 4 wherein a solubilizing agent is additionally present.

6. The process of claim 5 wherein the solubilizing agent is a phase-transfer catalyst.

7. The process of claim 4 wherein the initiator is lithium chloride.

8. The process of claim 1 wherein X is chloro.

9. The process of claim 8 wherein the β-haloalkyl carbonate is a 2-chloroethyl β-haloalkyl carbonate.

10. The process of claim 9 wherein the β-haloalkyl carbonate is 2-chloroethyl 1-chloro-2-propyl carbonate or 2-chloroethyl 1,3-dichloro-2-propyl carbonate.

* * * * *